United States Patent
Saiki et al.

(10) Patent No.: US 8,093,323 B2
(45) Date of Patent: Jan. 10, 2012

(54) METHOD FOR MANUFACTURING A BIS(SILATRANYLALKYL) POLYSULFIDE, METHOD FOR MANUFACTURING A MIXTURE OF BIS(SILATRANYLALKYL) POLYSULFIDE ETC., A MIXTURE OF BIS(SILATRANYLALKYL) POLYSULFIDE ETC., AND RUBBER COMPOSITION

(75) Inventors: Takeaki Saiki, Hiratsuka (JP); Makoto Iwai, Ichihara (JP); Anil Kumar Tomar, Midland, MI (US)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 29 days.

(21) Appl. No.: 12/522,835

(22) PCT Filed: Jan. 11, 2008

(86) PCT No.: PCT/JP2008/050659
§ 371 (c)(1),
(2), (4) Date: Jan. 15, 2010

(87) PCT Pub. No.: WO2008/084885
PCT Pub. Date: Jul. 17, 2008

(65) Prior Publication Data
US 2010/0120950 A1  May 13, 2010

(30) Foreign Application Priority Data
Jan. 12, 2007 (JP) .................. 2007-004762

(51) Int. Cl.
*C08K 5/24* (2006.01)
*C08K 5/00* (2006.01)
(52) U.S. Cl. ........................... 524/262; 524/87
(58) Field of Classification Search .............. 524/262
See application file for complete search history.

(56) References Cited

U.S. PATENT DOCUMENTS

| 3,997,581 A | 12/1976 | Pletka et al. |
| 4,129,585 A | 12/1978 | Buder et al. |
| 6,399,706 B1 | 6/2002 | Obrecht et al. |
| 2009/0221751 A1* | 9/2009 | Hasse et al. .................. 525/102 |

FOREIGN PATENT DOCUMENTS

| JP | 50108225 A | 8/1975 |
| JP | 2001031798 A | 2/2001 |
| WO | WO 2007/085521 A1 | 8/2007 |

OTHER PUBLICATIONS

English equivalent for JP 50108225 extracted from espacenet.com database, dated Nov. 30, 2009, 9 pages.
English language translation and abstract for JP 2001-031798 extracted from PAJ database, dated Nov. 30, 2009, 47 pages.
PCT International Search Report for PCT/JP2008/050659, dated Apr. 18, 2008, 3 pages.

* cited by examiner

*Primary Examiner* — Ling Choi
*Assistant Examiner* — Hui Chin
(74) *Attorney, Agent, or Firm* — Howard & Howard Attorneys PLLC

(57) ABSTRACT

A method for manufacturing a bis(silatranylalkyl) polysulfide by heating a bis(trialkoxysilylalkyl) polysulfide and triethanolamine in the presence of a catalytic quantity of an alkali-metal alcoholate, thus substituting all Si-bonded alkoxy groups of the bis(trialkoxysilylalkyl) polysulfide with a $(OCH_2CH_2)_3N$ group; a method for the preparation of a mixture of a bis(silatranylalkyl) polysulfide and a (silatranyalkyl)(trialkoxysilyl) disulfide or a mixture of a bis(silatranylalkyl) polysulfide, a (silatranylalkyl)(trialkoxysilyl) disulfide, and a bis(trialkoxysilylalkyl) polysulfide by heating a bis(trialkoxysilylalkyl) polysulfide and triethanolamine in the presence of a catalytic quantity of an alkali-metal alcoholate, thus substituting a part of Si-bonded alkoxy groups of the bis(trialkoxysilylalkyl) polysulfide with a $(OCH_2CH_2)_3N$ group; a mixture of a bis(silatranylalkyl) polysulfide and a (silatranylalkyl)(trialkoxysilyl) disulfide; a mixture of a bis (silatranylalkyl) polysulfide, a (silatranylalkyl)(trialkoxysilyl) disulfide, and a bis(trialkoxysilylalkyl) polysulfide; and a rubber composition containing the aforementioned mixture.

12 Claims, 3 Drawing Sheets

METHOD FOR MANUFACTURING A BIS(SILATRANYLALKYL) POLYSULFIDE, METHOD FOR MANUFACTURING A MIXTURE OF BIS(SILATRANYLALKYL) POLYSULFIDE ETC., A MIXTURE OF BIS(SILATRANYLALKYL) POLYSULFIDE ETC., AND RUBBER COMPOSITION

RELATED APPLICATIONS

This application claims priority to and all the advantages of International Patent Application No. PCT/JP2008/050659, filed on Jan. 11, 2008, which claims priority to Japanese Patent Application No. 2007-004762 filed on Jan. 12, 2007.

TECHNICAL FIELD

The present invention relates to a novel method for manufacturing a bis(silatranylalkyl) polysulfide; to a method for manufacturing a mixture of a bis(silatranylalkyl) polysulfide and a (silatranylalkyl)(trialkoxysilylalkyl) polysulfide; to a method for manufacturing a mixture of a bis(silatranylalkyl) polysulfide, a (silatranylalkyl)(trialkoxysilylalkyl) polysulfide, and a bis(trialkoxysilylalkyl) polysulfide; to a mixture of a bis(silatranylalkyl) polysulfide and a (silatranylalkyl)(trialkoxysilylalkyl) polysulfide; to a mixture of a bis(silatranylalkyl) polysulfide, a (silatranylalkyl)(trialkoxysilylalkyl) polysulfide, and a bis(trialkoxysilylalkyl) polysulfide; and to a rubber composition containing the aforementioned mixture.

BACKGROUND ART

A bis(silatranylalkyl) polysulfide and a method for manufacturing thereof are known from the published literature (see Patent Literature 1 (Japanese Unexamined Patent Application Publication {hereinafter referred to as "Kokai"} S50-108225, i.e., JP50-108225A), Patent Reference 2 (Kokai S60-33838, i.e., JP60-33838A), and Patent Reference 3 (Kokai 2001-31798, i.e., JP 2001-31798A)).

Example 13 added to the specification of Patent Reference 2 after the publication of the application describes synthesis of a bis(silatranylpropyl) tetrasulfide by mixing 2 moles of a silatranylpropylmercaptane with 3 moles of a sulfur powder under heating conditions.

This synthesis develops hydrogen sulfide, which normally is in a gaseous state and is characterized by very high toxicity. Therefore, the aforementioned method is associated with such problems as the use of synthesis equipment that prevents leakage of the generated hydrogen sulfide into the environment and the necessity of constantly wearing an antitoxic mask.

Example 13 of Patent Reference 2 describes a synthesized bis(silatranylpropyl) tetrasulfide, which is a white crystalline substance having no melting point. SILATRAN (OS34=Si79), which is the same as the aforementioned bis(silatranylpropyl) tetrasulfide, were mixed with a natural rubber, active silicic acid, or the like, the mixture was vulcanized, and physical properties of the product were measured. However, since the bis(silatranylpropyl) tetrasulfide is a crystalline substance having no melting point, dispersion thereof in such substances as a natural rubber or synthetic rubber and a silica filler presents a problem, even when the mixture is kneaded with application of a shear force, e.g., in a two-roll mill.

SUMMARY OF THE INVENTION

Based on a thorough study aimed at the solution of the above-described problems of the prior art, the inventors herein have found that if a bis(trialkoxysilylalkyl) polysulfide and a triethanolamine are heated in the presence of a specific catalyst with the resulting substitution of alkoxy groups with silatranyl group, then the by-product which is evolved in this process is merely an alcohol. The process is especially safe for the environment when alkoxy groups are represented by ethoxy groups, since in this case the developed by-product is ethanol which is an alcohol of high environmental safety.

The inventors also noticed that partial substitution of alkoxy groups of the bis(trialkoxysilylalkyl) polysulfide with silatranyl groups facilitates mixing with rubbers, silica fillers, and the like.

In view of the above, it is an object of the present invention to provide a new manufacturing method which does not use sulfur as a starting material, and does not generate toxic hydrogen sulfide during synthesis of the bis(silatranylalkyl) polysulfide. It is another object to provide an intermediate reaction mixture of a bis(trialkoxysilylalkyl) polysulfide and a bis(silatranylalkyl) polysulfide, as well as a method of the preparation of the aforementioned mixture.

The present invention relates to a method for manufacturing a bis(silatranylalkyl) polysulfide represented by the general formula (3):

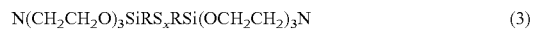
$$N(CH_2CH_2O)_3SiRS_xRSi(OCH_2CH_2)_3N \quad (3)$$

(wherein R is an alkylene group having 1 to 10 carbon atoms, and "x" is a number from 2 to 8), to a mixture of a bis(silatranylalkyl) polysulfide represented by the general formula (3):

$$N(CH_2CH_2O)_3SiRS_xRSi(OCH_2CH_2)_3N \quad (3)$$

(wherein R is an alkylene group having 1 to 10 carbon atoms and "x" is a number from 2 to 8) and a (silatranylalkyl)(trialkoxysilylalkyl) polysulfide represented by the general formula (4):

$$N(CH_2CH_2O)_3SiRS_xRSi(OR^1)_3 \quad (4)$$

(wherein R and "x" are the same as defined above, and $R^1$ is an alkyl group having 1 to 4 carbon atoms);

to a mixture of a bis(silatranylalkyl) polysulfide represented by the general formula (3):

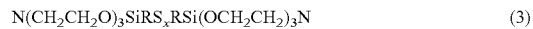
$$N(CH_2CH_2O)_3SiRS_xRSi(OCH_2CH_2)_3N \quad (3)$$

(wherein R is an alkylene group having 1 to 10 carbon atoms, and "x" is a number from 2 to 8), a (silatranylalkyl)(trialkoxysilylalkyl) polysulfide represented by the general formula (4):

$$N(CH_2CH_2O)_3SiRS_xRSi(OR^1)_3 \quad (4)$$

(wherein R and "x" are the same as defined above and $R^1$ is an alkyl group having 1 to 4 carbon atoms), and a bis(trialkoxysilylalkyl) polysulfide represented by the general formula (1):

$$(R^1O)_3SiRS_xRSi(OR^1)_3 \quad (1)$$

(wherein R, $R^1$, and "x" are the same as defined above), by heating a bis(trialkoxysilylalkyl) polysulfide represented by the general formula (1):

$$(R^1O)_3SiRS_xRSi(OR^1)_3 \quad (1)$$

(wherein R and "x" are the same as defined above, and $R^1$ is an alkyl group having 1 to 4 carbon atoms) and a triethanolamine represented by the formula (2):

$$(HOCH_2CH_2)_3N \quad (2)$$

in the presence of an alkali metal alcoholate used in a catalytic quantity; and to a rubber composition containing the aforementioned mixture.

DISCLOSURE OF THE INVENTION

Figure 1:
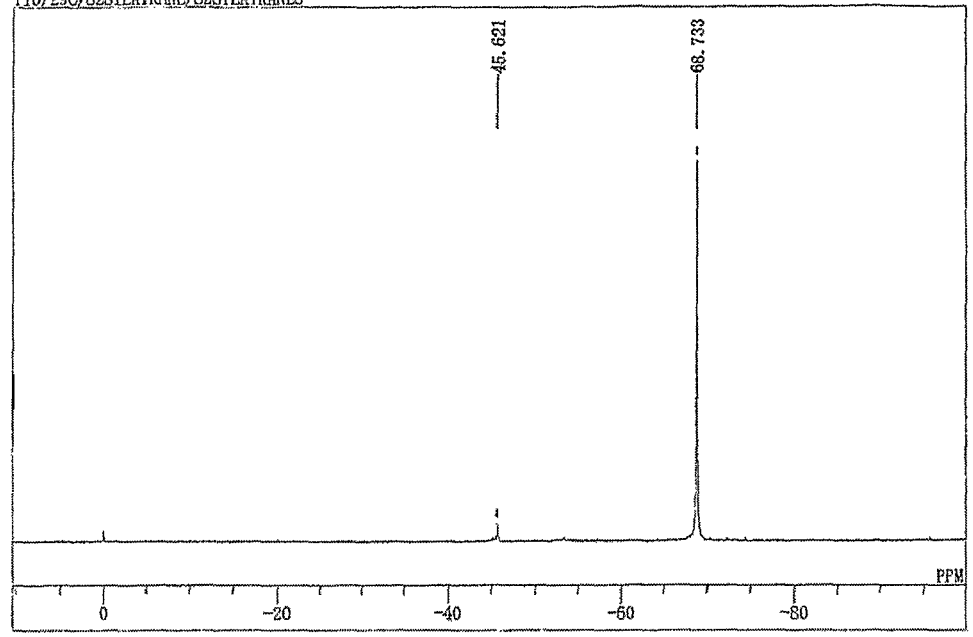
FIG. 1 illustrates a $^{29}$Si-NMR chart for the bis(silatranylpropyl) disulfide synthesized in EXAMPLE 1.
Figure 2:
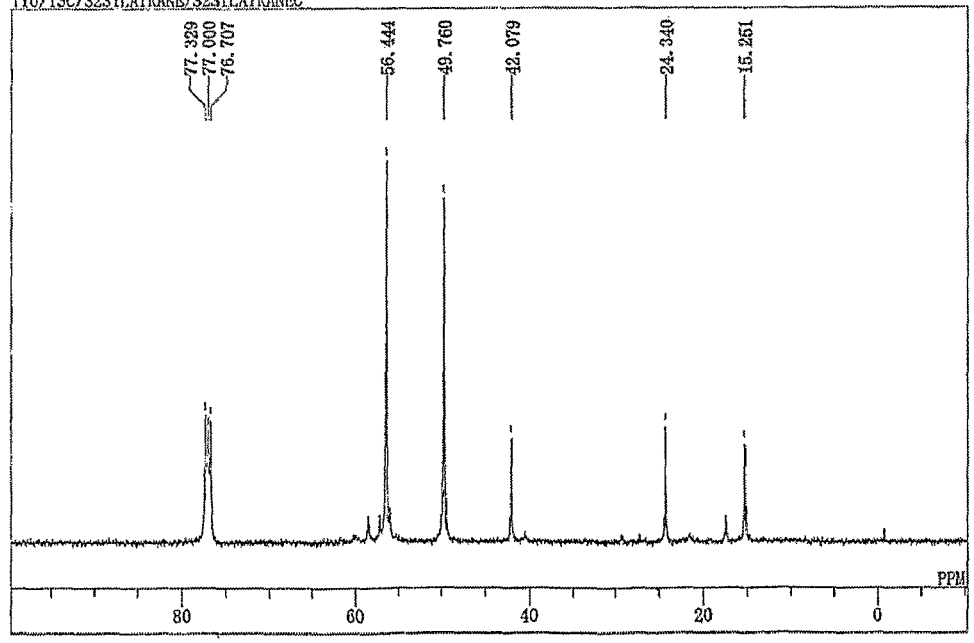
FIG. 2 illustrates a $^{13}$C-NMR chart for the bis(silatranylpropyl) disulfide synthesized in EXAMPLE 1.
Figure 3:
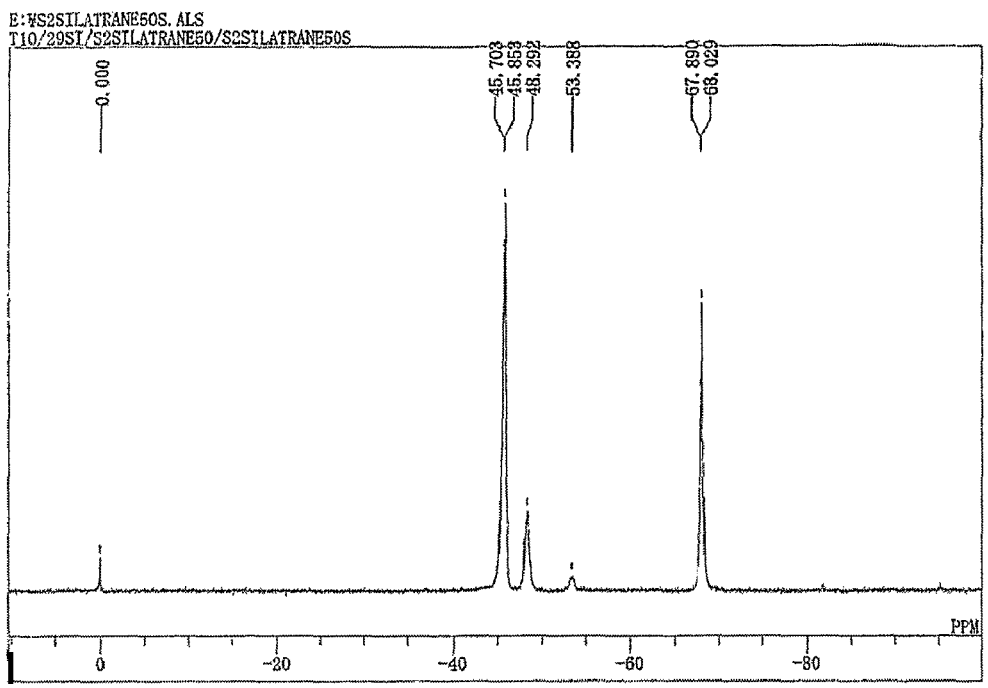
FIG. 3 illustrates a $^{29}$Si-NMR chart for the mixture of the bis(silatranylpropyl) disulfide, (silatranylpropyl)(triethoxysilylpropyl) disulfide, and bis(triethoxysilylpropyl) disulfide synthesized in EXAMPLE 2.
Figure 4:
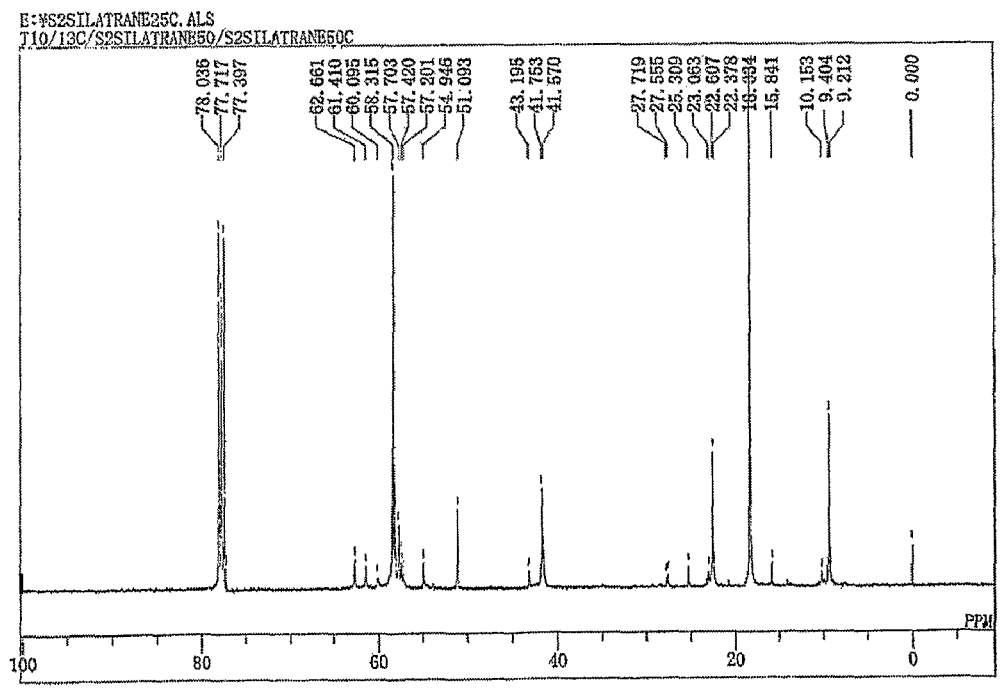
FIG. 4 illustrates a $^{13}$C-NMR chart for the mixture of the bis(silatranylpropyl) disulfide, (silatranylpropyl)(triethoxysilylpropyl) disulfide, and bis(triethoxysilylpropyl) disulfide synthesized in EXAMPLE 2.
Figure 5:
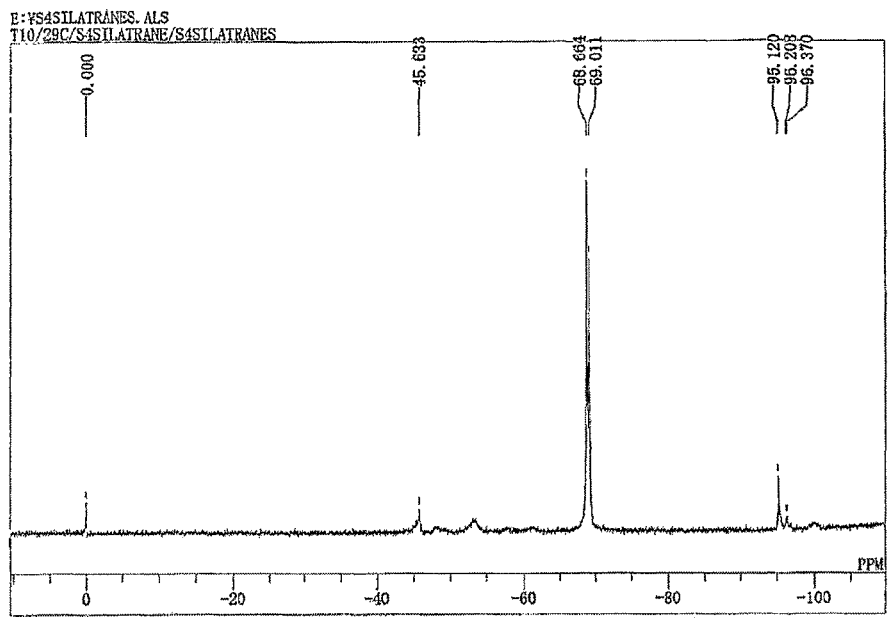
FIG. 5 illustrates a $^{29}$Si-NMR chart for the bis(silatranylpropyl) tetrasulfide synthesized in EXAMPLE 4.
Figure 6:
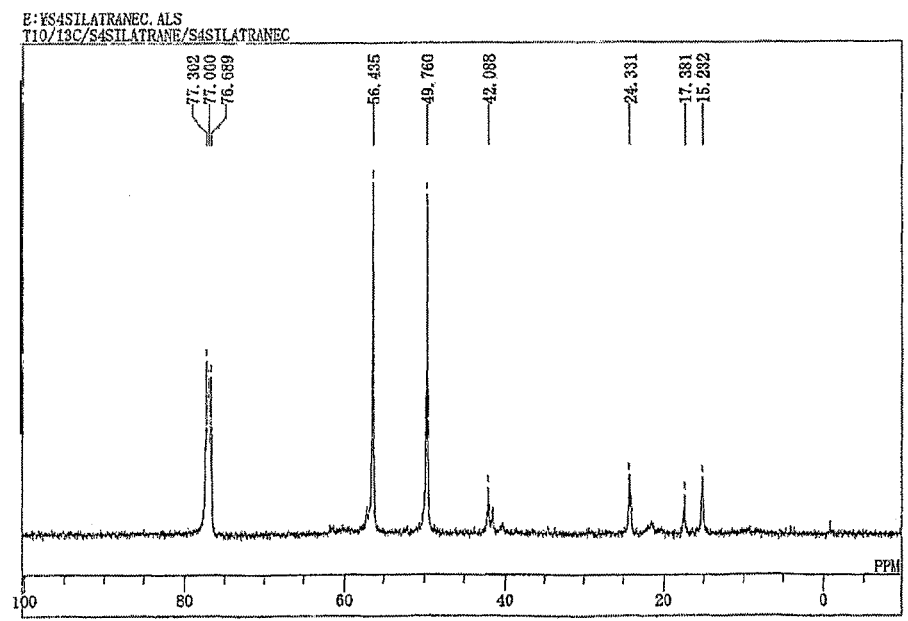
FIG. 6 illustrates a $^{13}$C-NMR chart for the bis(silatranylpropyl) tetrasulfide synthesized in EXAMPLE 4.

The present invention relate to the following;

[1] A method for manufacturing a bis(silatranylalkyl) polysulfide represented by the general formula (3):

$$N(CH_2CH_2O)_3SiRS_xRSi(OCH_2CH_2)_3N \quad (3)$$

(wherein R is an alkylene group having 1 to 10 carbon atoms, and "x" is a number from 2 to 8), the method being characterized by heating a bis(trialkoxysilylalkyl) polysulfide represented by the general formula (1):

$$(R^1O)_3SiRS_xRSi(OR^1)_3 \quad (1)$$

(wherein R and "x" are the same as defined above, and $R^1$ is an alkyl group having 1 to 4 carbon atoms) and a triethanolamine represented by the formula (2):

$$(HOCH_2CH_2)_3N \quad (2)$$

in the presence of an alkali metal alcoholate used in a catalytic quantity, thus substituting all Si-bonded $(OR^1)_3$ groups of the bis(trialkoxysilylalkyl) polysulfide represented by the general formula (1) with a group represented by the formula: $(OCH_2CH_2)_3N$.

[2] A method for manufacturing a mixture of a bis(silatranylalkyl) polysulfide represented by the general formula (3):

$$N(CH_2CH_2O)_3SiRS_xRSi(OCH_2CH_2)_3N \quad (3)$$

(wherein R is an alkylene group having 1 to 10 carbon atoms and "x" is a number from 2 to 8) and a (silatranylalkyl)(trialkoxysilylalkyl) polysulfide represented by the general formula (4):

$$N(CH_2CH_2O)_3SiRS_xRSi(OR^1)_3 \quad (4)$$

(wherein R and "x" are the same as defined above, and $R^1$ is an alkyl group having 1 to 4 carbon atoms), the method being characterized by heating a bis(trialkoxysilylalkyl) polysulfide represented by the general formula (1):

$$(R^1O)_3SiRS_xRSi(OR^1)_3 \quad (1)$$

(wherein R, $R^1$, and "x" are the same as defined above) and a triethanolamine represented by the formula (2):

$$(HOCH_2CH_2)_3N \quad (2)$$

in the presence of an alkali metal alcoholate used in a catalytic quantity, thus substituting a part of Si-bonded $(OR^1)_3$ groups of the bis(trialkoxysilylalkyl) polysulfide represented by the general formula (1) with a group represented by the formula: $(OCH_2CH_2)_3N$.

[3] A method for manufacturing a mixture of a bis(silatranylalkyl) polysulfide represented by the general formula (3):

$$N(CH_2CH_2O)_3SiRS_xRSi(OCH_2CH_2)_3N \quad (3)$$

(wherein R is an alkylene group having 1 to 10 carbon atoms, and "x" is a number from 2 to 8), a (silatranylalkyl)(trialkoxysilylalkyl) polysulfide represented by the general formula (4):

$$N(CH_2CH_2O)_3SiRS_xRSi(OR^1)_3 \quad (4)$$

(wherein R and "x" are the same as defined above and $R^1$ is an alkyl group having 1 to 4 carbon atoms), and a bis(trialkoxysilylalkyl) polysulfide represented by the general formula (1):

$$(R^1O)_3SiRS_xRSi(OR^1)_3 \quad (1)$$

(wherein R, $R^1$, and "x" are the same as defined above), the method being characterized by heating a bis(trialkoxysilylalkyl) polysulfide represented by the general formula (1):

$$(R^1O)_3SiRS_xRSi(OR^1)_3 \quad (1)$$

(wherein R, $R^1$, and "x" are the same as defined above) and a triethanolamine represented by the formula (2):

$$(HOCH_2CH_2)_3N \quad (2)$$

in the presence of an alkali metal alcoholate used in a catalytic quantity, thus substituting a part of Si-bonded $(OR^1)_3$ groups of the bis(trialkoxysilylalkyl) polysulfide represented by the general formula (1) with a group represented by the formula: $(OCH_2CH_2)_3N$.

[4] A mixture of a bis(silatranylalkyl) polysulfide represented by the general formula (3):

$$N(CH_2CH_2O)_3SiRS_xRSi(OCH_2CH_2)_3N \quad (3)$$

(wherein R is an alkylene group having 1 to 10 carbon atoms, and "x" is a number from 2 to 8) and a (silatranylalkyl)(trialkoxysilylalkyl) polysulfide represented by the general formula (4):

$$N(CH_2CH_2O)_3SiRS_xRSi(OR^1)_3 \quad (4)$$

(wherein R and "x" are the same as defined above, and $R^1$ is an alkyl group having 1 to 4 carbon atoms).

[5] A mixture of a bis(silatranylalkyl) polysulfide represented by the general formula (3):

$$N(CH_2CH_2O)_3SiRS_xRSi(OCH_2CH_2)_3N \quad (3)$$

(wherein R is an alkylene group having 1 to 10 carbon atoms, and "x" is a number from 2 to 8), a (silatranylalkyl)(trialkoxysilylalkyl) polysulfide represented by the general formula (4):

$$N(CH_2CH_2O)_3SiRS_xRSi(OR^1)_3 \quad (4)$$

(wherein R and "x" are the same as defined above, and $R^1$ is an alkyl group having 1 to 4 carbon atoms), and a bis(trialkoxysilylalkyl) polysulfide represented by the general formula (1):

$$(R^1O)_3SiRS_xRSi(OR^1)_3 \quad (1)$$

(wherein R, $R^1$, and "x" are the same as defined above).

[6] A rubber composition comprising:
100 parts by weight of an uncured organic rubber (A),
5.0 to 150 parts by weight of a silica filler (B), and the mixture (C) claimed in [4] or [5] which is contained in an amount of 0.1 to 50 wt. % of the weight of component (B).

[7] A rubber composition comprising:
100 parts by weight of an uncured organic rubber (A),
5.0 to 150 parts by weight of silica filler (B),
0.1 to 80 parts by weight of carbon black (D), and
the mixture (C) claimed in [4] or [5] which is contained in an amount of 0.1 to 50 wt. % of the total weight of components (B) and (D).

The method of the present invention for synthesis of the bis(silatranylalkyl) polysulfide is highly safe since it does not use sulfur as a starting material and does not generate toxic hydrogen sulfide in the synthesis process.

The method of the present invention for manufacturing a mixture of a bis(silatranylalkyl) polysulfide and a (silatranylalkyl)(trialkoxysilylalkyl) polysulfide is highly safe, since it does not use sulfur as a starting material and does not generate toxic hydrogen sulfide in the manufacturing process.

The method of the present invention for manufacturing of a mixture of a bis(silatranylalkyl) polysulfide, a (silatranylalkyl)(trialkoxysilylalkyl) polysulfide, and bis(trialkoxysilylalkyl) polysulfide, since it does not use sulfur as a starting material and does not generate toxic hydrogen sulfide in the manufacturing process.

The mixtures of the present invention are intermediate reaction products between the aforementioned bis(silatranylalkyl) polysulfide and bis(trialkoxysilylalkyl) polysulfide, which can be easily mixed with a rubber, a silica filler, and the like, since the mixtures are liquid at ambient temperature.

A vulcanizate of the rubber composition of the present invention has improved properties.

BEST MODE FOR CARRYING OUT THE INVENTION

The method of the present invention for manufacturing a bis(silatranylalkyl) polysulfide represented by the general formula (3):

$$N(CH_2CH_2O)_3SiRS_xRSi(OCH_2CH_2)_3N \quad (3)$$

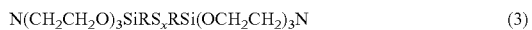

(wherein R is an alkylene group having 1 to 10 carbon atoms, and "x" is a number from 2 to 8), the method being characterized is characterized by heating a bis(trialkoxysilylalkyl) polysulfide represented by the general formula (1):

$$(R^1O)_3SiRS_xRSi(OR^1)_3 \quad (1)$$

(wherein R and "x" are the same as defined above, and $R^1$ is an alkyl group having 1 to 4 carbon atoms) and a triethanolamine represented by the formula (2):

$$(HOCH_2CH_2)_3N \quad (2)$$

in the presence of an alkali metal alcoholate used in a catalytic quantity, thus substituting a part of Si-bonded $(OR^1)_3$ groups of the bis(trialkoxysilylalkyl) polysulfide represented by the general formula (1) with a groups represented by the formula: $(OCH_2CH_2)_3N$.

In the bis(silatranylalkyl) polysulfide represented by the general formula (3):

$$N(CH_2CH_2O)_3SiRS_xRSi(OCH_2CH_2)_3N \quad (3)$$

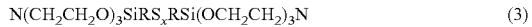

(wherein R is an alkylene group having 1 to 10 carbon atoms, and "x" is a number from 2 to 8), which is the target product of the manufacturing procedure, alkylene groups having 1 to 10 carbon atoms bond to sulfur atoms on both ends of the polysulfide that has 2 to 8 sulfur atoms, and silicon atoms of the silatranyl groups bond to carbon atoms on the terminals of the aforementioned alkylene groups.

In the above formula, R represents alkylene groups having 1 to 10 carbon atoms. These alkylene groups can be exemplified by ethylene, propylene, butylene, pentylene, hexylene, heptylene, and octylene groups. Normally, propylene to decylene groups have a linear molecular structure, but may also have a branched or cyclic structure. From the viewpoint of ease of production, it is advantageous to use propylene or butylene with a linear or branched molecular structure. From the viewpoint of ease of production, it is recommended to have 2 to 4 sulfur atoms.

The following are specific examples of the bis(silatranylalkyl) polysulfide: bis(silatranylethyl) disulfide, bis(silatranylethyl) tetrasulfide, bis(silatranylpropyl) disulfide, bis(silatranylpropyl) tetrasulfide, bis(silatranylbutyl) tetrasulfide, bis(silatranylpropyl) hexylsulfide, and bis(silatranylbutyl) hexylsulfide.

The bis(trialkoxysilylalkyl) polysulfide represented by the general formula (1):

$$(R^1O)_3SiRS_xRSi(OR^1)_3 \quad (1)$$

(wherein R designates an alkylene group having 1 to 10 alkylene atoms, $R^1$ is an alkyl group having 1 to 4 carbon atoms, and "x" is a number from 2 to 8) is a starting material used for the production. In the above formula, $R^1$ is an alkyl group having 1 to 4 carbon atoms. Such an alkyl group can be exemplified by methyl, ethyl, propyl, and butyl groups. Normally, the propyl and butyl groups have a linear molecular structure but a branched structure is also possible. From the viewpoint of ease of substituted with silatranyl group the use of methyl groups and, especially, ethyl groups, is preferable. The alkylene groups designated by R can be exemplified by ethylene, propylene, butylene, pentylene, hexylene, heptylene, and octylene groups. Normally, the groups from propylene to decylene have a liner molecular structure, but may also have a branched or cyclic structure as well. The propylene group and butylene group with the linear or branched molecular structure are preferable for ease of production.

The following are specific examples of the bis(trialkoxysilylalkyl) polysulfide represented by the general formula (1): bis(trimethoxysilylpropyl) disulfide, bis(trimethoxysilylbutyl) disulfide, bis(triethoxysilylpropyl) disulfide, bis(triethoxysilylbutyl) disulfide, bis(trimethoxysilylpropyl) tetrasulfide, bis(triethoxysilylpropyl) tetrasulfide, bis(tripropoxysilylpropyl) tetrasulfide, bis(trimethoxysilylbutyl) tetrasulfide, bis(triethoxysilylbutyl) tetrasulfide, bis(tripropoxysilylbutyl) tetrasulfide, bis(trimethoxysilylpropyl) hexylsulfide, bis(triethoxysilylpropyl) hexylsulfide, and bis(trimethoxysilylbutyl) hexylsulfide.

The triethanolamine, which is a starting material for the product of the present invention and is represented by the formula (2):

$$(HOCH_2CH_2)_3N, \quad (2)$$

is reacted with the $(R^1O)_3Si$ groups of the bis(trialkoxysilylalkyl) polysulfide represented by the general formula (1), whereby three moles of $R^1OH$ groups are generated and silatranyl groups are formed. Since the bis(trialkoxysilylalkyl) polysulfide represented by the general formula (1) contains in one molecule two $(R^1O)_3Si$ groups, at least two moles of the triethanolamine are required. In order to complete the substitution reaction, it is recommended to provide 2.0 to 2.4 moles of triethanolamine per 1 mole of the bis(trialkoxysilylalkyl) polysulfide represented by the general formula (1).

Since mere heating of the bis(trialkoxysilylalkyl) polysulfide represented by the general formula (1) and triethanolamine is not sufficient for rapid substitution, the reaction should be carried out in the presence of an alkali metal alcoholate used in a catalytic quantity. The alkali metal alcoholate can be represented by sodium methoxide, sodium ethoxide, potassium methoxide, potassium ethoxide, or lithium ethoxide. It is recommended to use alkali metal alcoholate in the amount of 0.1 to 5.0 mole % per 1 mole of the bis(trialkoxysilylalkyl) polysulfide represented by the general formula (1). Since the alkali metal alcoholate is a solid, it is added to the bis(trialkoxysilylalkyl) polysulfide represented by the general formula (1) preferably in a form of an alcohol solution.

The reaction between the bis(trialkoxysilylalkyl) polysulfide represented by the general formula (1) and the triethanolamine can be carried out for about 30 min. to 4 hours under a reduced pressure and at a temperature in the range of 120 to 180° C. Upon completion of the reaction, the alcohol developed in the reaction is removed by distillation under heating and reduced-pressure conditions. If the product of the reaction contains residual triethanolamine that has been supplied to the reaction, it also can be removed together with the alcohol by distillation under heating and reduced-pressure conditions.

A mixture of the present invention is composed of a bis(silatranylalkyl) polysulfide represented by the general formula (3):

$$N(CH_2CH_2O)_3SiRS_xRSi(OCH_2CH_2)_3N \qquad (3)$$

(wherein R is an alkylene group having 1 to 10 carbon atoms, and "x" is a number from 2 to 8) and a (silatranylalkyl)(trialkoxysilylalkyl) polysulfide represented by the general formula (4):

$$N(CH_2CH_2O)_3SiRS_xRSi(OR^1)_3 \qquad (4)$$

(wherein R and "x" are the same as defined above, and $R^1$ is an alkyl group having 1 to 4 carbon atoms).

Another mixture of the present invention is composed of a mixture of a bis(silatranylalkyl) polysulfide represented by the general formula (3):

$$N(CH_2CH_2O)_3SiRS_xRSi(OCH_2CH_2)_3N \qquad (3)$$

(wherein R is an alkylene group having 1 to 10 carbon atoms, and "x" is a number from 2 to 8), a (silatranylalkyl)(trialkoxysilylalkyl) polysulfide represented by the general formula (4):

$$N(CH_2CH_2O)_3SiRS_xRSi(OR^1)_3 \qquad (4)$$

(wherein R and "x" are the same as defined above, and $R^1$ is an alkyl group having 1 to 4 carbon atoms), and a bis(trialkoxysilylalkyl) polysulfide represented by the general formula (1):

$$(R^1O)_3SiRS_xRSi(OR^1)_3 \qquad (1)$$

(wherein R, $R^1$, and "x" are the same as defined above).

The mixture composed of a bis(silatranylalkyl) polysulfide represented by the general formula (3):

$$N(CH_2CH_2O)_3SiRS_xRSi(OCH_2CH_2)_3N \qquad (3)$$

(wherein R is an alkylene group having 1 to 10 carbon atoms, and "x" is a number from 2 to 8) and a (silatranylalkyl)(trialkoxysilylalkyl) polysulfide represented by the general formula (4):

$$N(CH_2CH_2O)_3SiRS_xRSi(OR^1)_3 \qquad (4)$$

(wherein R and "x" are the same as defined above, and $R^1$ is an alkyl group having 1 to 4 carbon atoms) or the mixture composed of a bis(silatranylalkyl) polysulfide represented by the general formula (3):

$$N(CH_2CH_2O)_3SiRS_xRSi(OCH_2CH_2)_3N \qquad (3)$$

(wherein R is an alkylene group having 1 to 10 carbon atoms, and "x" is a number from 2 to 8), a (silatranylalkyl)(trialkoxysilylalkyl) polysulfide represented by the general formula (4):

$$N(CH_2CH_2O)_3SiRS_xRSi(OR^1)_3 \qquad (4)$$

(wherein R, $R^1$, and "x" are the same as defined above), and a bis(trialkoxysilylalkyl) polysulfide represented by the general formula (1):

$$(R^1O)_3SiRS_xRSi(OR^1)_3 \qquad (1)$$

(wherein R, $R^1$, and "x" are the same as defined above) can be produced when the bis(trialkoxysilylalkyl) polysulfide represented by the general formula (1):

$$(R^1O)_3SiRS_xRSi(OR^1)_3 \qquad (1)$$

(wherein the R, $R^1$, and "x" are the same as defined above) and the triethanolamine represented by the formula (2):

$$(HOCH_2CH_2)_3N$$

are heated in the presence of an alkali metal alcoholate used in a catalytic quantity, whereby a part of the silicon-bonded $(OR^1)_3$ groups of the bis(trialkoxysilylalkyl) polysulfide represented by the general formula (1) is substituted with a $(OCH_2CH_2)_3N$ group.

By providing less than 2.0 moles of the triethanolamine per 1 mole of the bis(trialkoxysilylalkyl) polysulfide represented by the general formula (1) in the aforementioned heating reaction, it becomes possible to substitute a part of silicon-bonded $(OR^1)_3$ groups with a $(OCH_2CH_2)_3N$ group. For example, when 1.75 moles of the triethanolamine per 1 mole of the bis(trialkoxysilylalkyl) polysulfide represented by the general formula (1) are provided to the reaction, it becomes possible to produce a mixture of almost equivalent quantities of the bis(silatranylalkyl) polysulfide represented by the general formula (3):

$$N(CH_2CH_2O)_3SiRS_xRSi(OCH_2CH_2)_3N \qquad (3)$$

(wherein R is an alkylene group having 1 to 10 carbon atoms, and "x" is a number from 2 to 8) and the (silatranylalkyl)(trialkoxysilylalkyl) polysulfide represented by the general formula (4):

$$N(CH_2CH_2O)_3SiRS_xRSi(OR^1)_3 \qquad (4)$$

(wherein and "x" are the same as defined above and $R^1$ is an alkyl group having 1 to 4 carbon atoms).

In order to prevent the bis(trialkoxysilylalkyl) polysulfide represented by the general formula (1) from remaining in the reaction product, it is recommended to supply triethanolamine to the reaction in an amount of 1.75 moles or more but 2.0 moles or less per 1 mole of the bis(trialkoxysilylalkyl) polysulfide represented by the general formula (1).

For example, when the reaction is carried out by supplying to the reaction 1.0 mole of the triethanolamine per 1.0 mole of the bis(trialkoxysilylalkyl) polysulfide represented by the general formula (1), then the mixture of the bis(silatranylalkyl) polysulfide represented by the general formula (3):

$$N(CH_2CH_2O)_3SiRS_xRSi(OCH_2CH_2)_3N \qquad (3)$$

(wherein R is an alkylene group having 1 to 10 carbon atoms, and "x" is a number from 2 to 8), the (silatranylalkyl)(trialkoxysilylalkyl) polysulfide represented by the general formula (4):

$$N(CH_2CH_2O)_3SiRS_xRSi(OR^1)_3 \qquad (4)$$

(wherein R and "x" are the same as defined above, and $R^1$ is an alkyl group having 1 to 4 carbon atoms), and the bis(trialkoxysilylalkyl) polysulfide represented by the general formula (1):

$$(R^1O)_3SiRS_xRSi(OR^1)_3 \qquad (1)$$

(wherein R, $R^1$, and "x" are the same as defined above) is obtained almost in a ratio of 1:2:1.

Appropriate rubber compositions to which the bis(silatranylalkyl) polysulfide or the aforementioned mixtures that have been produced by the method of the present invention are added may consist mainly of an uncured organic rubber (A) and a silica filler (B), or an uncured organic rubber (A), a silica filler (B), and a carbon black (D).

(A) An uncured organic rubber is usually referred to merely as "rubber". This component is an organic polymer that exhibits resiliency when vulcanized.

There are no special restrictions with regard to this uncured organic rubber, provided that it is suitable for manufacturing tires and especially tire treads. The appropriate uncured organic rubber comprises a highly unsaturated organic polymer compound, in particular, a diene-type polymer compound with an iodine number in the range of 20 to 450.

The uncured organic rubber is exemplified by an uncured styrene/butadiene copolymer rubber, uncured polybutadiene rubber, uncured isoprene/butadiene copolymer rubber, uncured styrene/isoprene copolymer rubber, uncured styrene/isoprene/butadiene copolymer rubber, uncured acrylonitrile/butadiene copolymer rubber, uncured polyisoprene rubber, uncured natural rubber, or a similar uncured conjugated diene-type rubber, uncured chloroprene rubber, and uncured partially-hydrogenated diene-type rubber.

In the composition of the present invention, silica filler (B) and carbon black (D) are fillers that are used for reinforcing the rubber obtained after vulcanization. A silica filler may comprise reinforcing silica such as fumed silica (dry-process silica) or precipitated silica (wet-process silica). These fillers may be hydrophobized by treating their surfaces with an organic silicon compound such as hexamethyldisilazane, dimethyldichlorosilane, trimethylchlorosilane, or octamethyltetracyclosiloxane. Carbon black may comprise the one normally used for rubber reinforcement and may be represented, e.g., by furnace black, channel black, lamp black, thermal black, or acetylene black. Carbon black can be used in a pellet-type form or in the form of non-pelletized aggregated lumps.

Component (B) is contained in an amount of 5 to 150 parts by weight, preferably 10 to 100 parts by weight, and most preferably, 30 to 90 parts by weight per 100 parts by weight of component (A). When carbon black (D) is contained, it should be contained in an amount of 0.1 to 80 parts by weight and, preferably, 5 to 50 parts by weight per 100 parts by weight of component (A). However, the total weight of components (B) and (D) should not exceed 120 parts by weight per 100 weight of component (A). If the aforementioned filler is contained in amounts less than the recommended lower limit, the obtained rubber will not be sufficiently strong. If, on the other hand, the added amount exceeds the recommended range, this will create difficulties for mixing and kneading the fillers with component (A).

The bis(silatranylalkyl) polysulfide or the aforementioned mixtures containing this compound and obtained by the method of the present invention (hereinafter referred to as component (C)) is added to the rubber composition in an amount of 0.1 to 50 wt. %, preferably, 0.1 to 30 wt. % per weight of component (B), or in an amount of 0.1 to 50 wt. %, preferably, 0.1 to 30 wt. % per total weight of components (B) and (D).

Component (C) can be mixed with components (B) and (A) in the form of an alkyleneglycol or a polyalkyleneglycol solution. This improves dispersibility in components (A) and (B). Concentration of component (C) in the solution should be in the range of 30 to 95 wt. %.

Various methods can be used for mixing component (C) with other components. For example, component (C) can be pre-mixed with component (B) and then the mixture is added and mixed with component (A). Alternatively, component (C) can be added to a mixture of components (A) and (B).

If necessary, the rubber composition of the present invention may be combined with other conventional additives such as weight-increasing fillers, organic fibers, naphthene-type process oil or similar softeners, pigments, foaming agents, ultraviolet-ray absorbers, aging inhibitors, antioxidants, scorch inhibitors, waxes, etc. There are no special restrictions with regard to the amounts in which these additives can be added to the rubber composition, and the aforementioned amounts can be appropriately selected, provided that the additives in the selected amounts do not adversely affect tire performance.

The rubber composition containing component (C) of the present invention can be produced by methods known in the art. The components for the rubber composition can be uniformly mixed and kneaded in a Banbury mixer, two-axis roller, kneader-mixer, two-axis extruder, etc. During mixing, the rubber composition should have a temperature in the range of 120 to 180° C.

Vulcanization agents such as sulfur, insoluble sulfur, sulfur compound, etc., can be added to the composition in a two-roll mill, two-axis extruder, etc., for vulcanization and formation of tires, and especially tire treads. If necessary, vulcanization-assisting agents and vulcanization accelerators can also be added. The vulcanization assistants may comprise zinc oxide, stearic acid, etc. The vulcanization accelerators may comprise mercaptobenzothiazol (MBT), benzothiazyldisulfide (MBTS), N-tert-butyl-2-benzothiazolylsulfenamide (TBBS), N-cyclohexyl-2-benzothiazyl-sulfinamide (CBS), or similar thiazol-type accelerators. Because mixing may cause heating and premature vulcanization, mixing can be carried out with cooling.

The rubber composition that contains the vulcanization agent and if necessary other additives, is subjected to heating and molding in a mold. If necessary, after primary vulcanization, the vulcanizate can be subjected to a secondary vulcanization.

An example of the molded rubber products that can be obtained by vulcanizing the rubber composition that contains component (C) are tires such as automobile tires, aircraft tires, bicycle tires, etc., but the most preferable are passenger-car tires, truck tires, race-car tires, and aircraft tires. Other molded rubber products may comprise rubber-coated rollers, packings, rubber tubes, rubber sheets, rubber-coated wires, etc.

EXAMPLES

The present invention is further described with reference to practical examples and comparative examples. In the EXAMPLES, $^{29}$Si-NMR measurements of the bis(silatranylpropyl) disulfide; a mixture of the bis(silatranylpropyl) disulfide, the (silatranylpropyl)(triethoxysilylpropyl) disulfide, and the bis(triethoxysilylpropyl) disulfide; and the bis(silatranylpropyl) tetrasulfide were carried out in heavy deuteriumchloroform by using a JEOL JNM-EX400 (product of JEOL.CO.JP) spectrometer and employing tetramethylsilane as an internal reference.

The presence of silatranyl groups in the bis(silatranylpropyl) disulfide, the aforementioned mixture, and bis(silatranylpropyl) tetrasulfide was detected in the same manner as above by observing peaks in $^{29}$Si-NMR and $^{13}$C-NMR charts. The amounts of the bis(silatranylpropyl) disulfide, the (silatranylpropyl)(triethoxysilylpropyl) disulfide, and bis(triethoxysilylpropyl) disulfide were determined by calculating ratios of the starting materials. Weights are given in terms of wt. %. "Et" designates ethyl groups.

Example 1

A flask equipped with a stirrer, thermometer, and condenser was filled with 47.5 g (0.1 mole) of bis(triethoxysilylpropyl)

disulfide, 29.8 g (0.2 mole) of triethanolamine, and 0.34 g (0.001 mole) of a 20% ethanol solution of sodium ethylate. The mixture was then stirred for 2 hours at 150° C. while the pressure was reduced to 200 mmHg. After 2-hour stirring, the pressure was further reduced, the ethanol generated in the process was removed by distillation, and 50.1 g of the bis(silatranylpropyl) disulfide shown below were obtained with the yield of 99%.

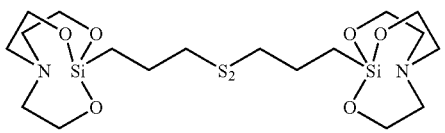

Example 2

A flask equipped with a stirrer, thermometer, and condenser was filled with 47.5 g (0.1 mole) of bis(triethoxysilylpropyl) disulfide, 14.9 g (0.1 mole) of triethanolamine, and 0.34 g (0.001 mole) of a 20% ethanol solution of sodium ethylate. The mixture was then stirred for 2 hours at 150° C. while the pressure was reduced to 200 mmHg. After 2-hour stirring, the pressure was further reduced, the ethanol generated in the process was removed by distillation, and 48.0 g of a mixture of the bis(silatranylpropyl) disulfide, the (silatranylpropyl)(triethoxysilylpropyl) disulfide, and the bis(triethoxysilylpropyl) disulfide shown below were obtained with the yield of 99%.

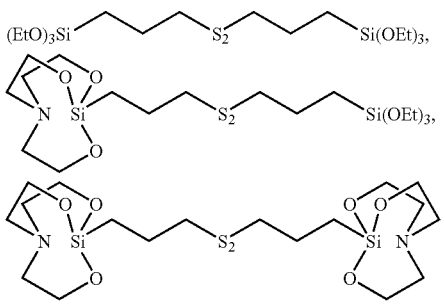

(In the above formula, silatranyl groups constitute 50 mole % of the sum of silatranyl groups and triethoxysilyl groups.)

Example 3

A flask equipped with a stirrer, thermometer, and condenser was filled with 47.5 g (0.1 mole) of bis(triethoxysilylpropyl) disulfide, 7.5 g (0.05 mole) of triethanolamine, and 0.34 g (0.001 mole) of a 20% ethanol solution of sodium ethylate. The mixture was then stirred for 2 hours at 150° C. while the pressure was reduced to 200 mmHg. After 2-hour stirring, the pressure was further reduced, the ethanol generated in the process was removed by distillation, and 47.8 g of a mixture of the bis(silatranylpropyl) disulfide, the (silatranylpropyl)(triethoxysilylpropyl) disulfide, and the bis(triethoxysilylpropyl) disulfide shown below were obtained with the yield of 99%.

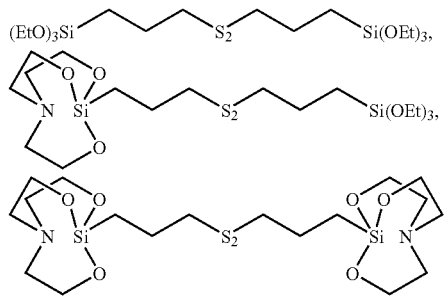

(In the above formula, silatranyl groups constitute 25 mole % of the sum of silatranyl groups and triethoxysilyl groups.)

Example 4

A flask equipped with a stirrer, thermometer, and condenser was filled with 53.9 g (0.1 mole) of bis(triethoxysilylpropyl) tetrasulfide, 29.8 g (0.2 mole) of triethanolamine, and 0.34 g (0.001 mole) of a 20% ethanol solution of sodium ethylate. The mixture was then stirred for 2 hours at 150° C. while the pressure was reduced to 200 mmHg. After 2-hour stirring, the pressure was further reduced, the ethanol generated in the process was removed by distillation, and 55.8 g of the bis(silatranylpropyl) tetrasulfide shown below were obtained with the yield of 98%.

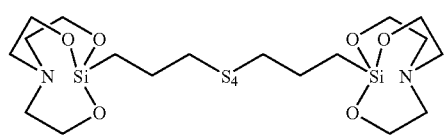

Application Example 1 and Referential Application Example 1

A rubber composition for specimen B and a rubber composition for specimen C composed of components shown in Table 1 were prepared.

TABLE 1

| Components | Application Example 1 Composition for Specimen B | Referential Application Example 1 Composition for Specimen C |
|---|---|---|
| SBR (JSR1500) | 100 | 100 |
| HAF Carbon (Asahi # 70) | 5 | 5 |
| Nipsil AQ | 40 | 40 |
| Zinc Oxide, Type 2 | 3 | 3 |
| Bis(silatranylpropyl) tetrasulfide of Practical Example 4 | 4 | — |
| Bis(triethoxysilylpropyl) tetrasulfide | — | 4 |
| Diethyleneglycol | — | 2.5 |
| Stearic Acid | 2 | 2 |
| NOCRAC 810-NA | 1 | 1 |
| NOCCELER-CZ | 1.2 | 1.2 |
| NOCCELER-D | 1.5 | 1.5 |
| Sulfur Powder | 1.5 | 1.5 |

A more detailed description of the aforementioned components is given below in Table 2.

TABLE 2

| | |
|---|---|
| SBR (JSR1500) | Emulsion-polymerized styrene butadiene rubber, product of JSR Co. Stabilizer: ST; Bonded Styrene: 23.5%; Mooney viscosity ML1 + 4 (100° C.): 52; Emulsifier: RA; Coagulant: salt-acid, Specific Gravity: 0.94 |
| Bis(triethoxysilylpropyl) tetrasulfide | Product of Dow Corning Toray Co., Ltd. Product name is Z-6940. |
| HAF Carbon (Asahi # 70) | product of Asahi Carbon Co, Ltd. average particle size: 28 nm, specific surface area: 77 $m^2$/g, iodine adsorption: 80 mg/g, DBP adsorption(A method): 101 ml/100 g, heating loss: 0.3%, volatile content: 1.3% |
| Nipsil AQ | Precipitated silica (microgranule-type highly active product), product of TOSOH SILICA CORPORATION |
| Zinc Oxide, Type 2 | Grain size: 0.2 to 0.6 μm; product of MISTUI MINING & SMELTING CO., LTD. |
| Stearic Acid | Product of NOF CORPORATION |
| NOCRAC 810-NA | NOCRAC is a registered trademark of Ouchi Saimo Trading Co., N-phenyl-N-isopropyl-p-phenylenediamine, Phenylisopropyl-p-phenylenediamine, 1-phenylamino-4-isopropylaminobenzene, product of OUCHI SHINKO CHEMICAL INDUSTRIAL, Aromatic secondary amine-type antiaging agent and crack-preventing agent for NR, IR, BR, SBR, NBR, CR |
| NOCCELER-CZ | NOCCELER-CZ-G NOCCELER is a registered trademark of Ouchi Saimo Trading Co., N-cyclohexyl-2-benzothiazolyl-sulfenamide, JIS K 6202, product of OUCHI SHINKO CHEMICAL INDUSTRIAL, sulfenamide-type delayed effective vulcanization accelerator for NR, IR, BR, SBR, NBR, CR |
| NOCCELER-D | NOCCELER-D-P, 1,3-diphenylguanidine, N,N'diphenylguanidine, product of OUCHI SHINKO CHEMICAL INDUSTRIAL, guanidine-type vulcanization accelerator for NR, IR, BR, SBR, NBR, CR |
| Sulfur Powder | Product of Kawagoe Chemical Co. |

In the preparation of the rubber composition, mixing and kneading of the components were carried out in accordance with JIS K6299 "Preparation of Test Pieces for Testing Rubber"

Mixing and Kneading Conditions (One-step kneading in a tightly sealed kneader)
  Test machine—Laboplast Mill—100C 100 type
  Rotor: B600 (Banbury type, 600 $cm^3$)
  Rotor speed: 50 rpm
  Filling rate: 70%
  Set temperature: 120° C.
  Maximal temperature at the exit: 150° C.
  Duration of kneading: 4 min.
    (Two-Stage Kneading: Roller-Type Kneading Machine)
  Roller dimensions: diameter. 8"×18"
  Front roller speed: 20 rpm
  Front/rear roller speed ratio: 1:1.5
Each aforementioned composition was vulcanized under the following condition.
  Sheet
    Test Piece A: 160° C.×11 min.
    Test Piece C: 160° C.×18 min.
  Block
    Test Piece A: 160° C.×16 min.
    Test Piece C: 160° C.×23 min.

Characteristics of the rubber compositions for aforementioned test pieces and characteristics of the rubbers obtained by vulcanizing the rubber compositions were measured under conditions given below. The results of measurements are shown in Table 3.

<Methods of Measuring Characteristics of Rubber Compositions and Rubbers>

1. Mooney Viscosity

This characteristic was measured in accordance with the provisions of JIS K6300 "Physical testing methods for unvulcanized rubber"
  Measurement temperature: 100° C.
  Die vulcanization test-A method
  Oscillation amplitude: ±1°, oscillation frequency: 1.67 Hz 2. Elongation (%)

This characteristic was measured in according with the provisions of JIS K6251 "Method of testing tensile strength of vulcanized rubber".
Specimen: JIS No. 3 for tensile test 3. Tear Strength (N/mm)

This characteristic was measured in according with the provisions of JIS K6252 "Method of testing tear strength of vulcanized rubber".
  Specimen: angle-shaped without slitting (perpendicular to grain direction).

4. Hardness (Durometer hardness)

This characteristic was measured in according with the provisions of JIS K6253 "Method of testing hardness of vulcanized rubber and thermoplastic rubber".

5. Worn Volume ($cm^3$)

This characteristic was measured by the Acron wear method test (A-2) in according with the provisions of JIS K6264 "Method of testing wear of vulcanized resin".
  Load: 44.1N (4.50 kgf)
  Angle: 10°
  Preliminary test: 500 revolutions
  Basic test: 1000 revolutions 6. Tan δ

This characteristic was measured in according with the provisions of JIS K7244-4 "Method of testing dynamic characteristics of plastics—Part 4: Tensile vibrations—Non-resonant vibration method".
  Measured items:
  dynamic storage modulus of elasticity E'
  dynamic loss modulus of elasticity E"

tangent of loss tan δ
Sample dimensions: 1 mm×5 mm×30 mm
Measurement mode: tensile mode
Measurement frequency: 10 Hz
Heating rate: 2° C./min
Measurement temperature: 0° C., 60° C.
Dynamic strain: 0.1%
Tester: Viscosity measuring instrument RSA-II, the product of Rheometrics Co.

7. Characteristic Balance

The ratio of aforementioned tan δ (0° C.) to tan δ (60° C.) is indicated as (0° C./60° C.). The greater is the ratio, the better is the tire balance (wet skidding and low fuel consumption properties).

Measurement results of Test Piece "B" and Test Piece "C" are shown in Table 3.

TABLE 3

| Type of test | Test conditions | Application Example 1 Test Piece "B" | Referential Application Example 1 Test Piece "C" |
|---|---|---|---|
| Mooney Viscosity Test | ML1 + 4 (100° C.) | 77 | 70 |
| Vulcanization test with the use of vibration-type vulcanization tester (curastometer, type III, 160° C.) | Minimal value (N · m) | 0.2 | 0.19 |
| | Maximal value (N · m) | 1.49 | 1.73 |
| | $T_{10}$ (min.) | 2.0 | 5.3 |
| | $T_{50}$ (min.) | 3.0 | 7.9 |
| | $T_{90}$ (min.) | 7.5 | 13.0 |
| Hardness test | Durometer hardness | A68 | A70 |
| Tensile test | Tensile strength (MPa) | 29.4 | 26.4 |
| | Elongation (%) | 610 | 500 |
| | 100% tensile stress (MPa) | 1.95 | 2.34 |
| | 200% tensile stress (MPa) | 4.23 | 5.68 |
| | 300% tensile stress (MPa) | 8.85 | 11.4 |
| | 400% tensile stress (MPa) | 13.3 | 18.4 |
| | 500% tensile stress (MPa) | 20.1 | 26.4 |
| Tear test | Tear strength (N/mm) | 58.0 | 59.4 |
| Wearability test (Acron system) | Wear volume (cm$^3$) | 0.012 | 0.021 |
| Viscoelasticity test | tan δ at 0° C. | 0.130 | 0.132 |
| | tan δ at 60° C. | 0.120 | 0.086 |
| | tan δ at 0° C./tan δ at 60° C. | 1.08 | 1.53 |

INDUSTRIAL APPLICABILITY

The method of the present invention for manufacturing a bis(silatranylalkyl) polysulfide is useful for manufacturing the bis(silatranylalkyl) polysulfide in a simple manner and with a high yield without generating hydrogen sulfide.

The method of the present invention for manufacturing a mixture of the bis(silatranylalkyl) polysulfide and a (silatranylalkyl)(trialkoxysilylalkyl) polysulfide is useful for manufacturing the mixture in a simple manner and with a high yield without generating hydrogen sulfide.

The method of the present invention for manufacturing a mixture of the bis(silatranylalkyl) polysulfide, a (silatranylalkyl)(trialkoxysilylalkyl) polysulfide, and bis(trialkoxysilylalkyl) polysulfide is useful for manufacturing the mixture in a simple manner and with a high yield without generating hydrogen sulfide.

The aforementioned mixture of the present invention is useful for adding to rubbers for improving properties.

The rubber composition containing the aforementioned mixture of the present invention is useful for manufacturing tires, specifically tire trades.

The invention claimed is:

1. A method for manufacturing a mixture which is liquid at ambient temperature and comprises a bis(silatranylalkyl) polysulfide represented by the general formula (3):

$$N(CH_2CH_2O)_3SiRS_xRSi(OCH_2CH_2)_3N \quad (3)$$

wherein R is an alkylene group having 1 to 10 carbon atoms and "x" is a number from 2 to 8, and a (silatranylalkyl)(trialkoxysilylalkyl) polysulfide represented by the general formula (4):

$$N(CH_2CH_2O)_3SiRS_xRSi(OR^1)_3 \quad (4)$$

wherein R and "x" are the same as defined above, and $R^1$ is an alkyl group having 1 to 4 carbon atoms, the method being characterized by heating a bis(trialkoxysilylalkyl) polysulfide represented by the general formula (1):

$$(R^1O)_3SiRS_xRSi(OR^1)_3 \quad (1)$$

wherein R, $R^1$, and "x" are the same as defined above, and a triethanolamine represented by the formula (2):

$$(HOCH_2CH_2)_3N \quad (2)$$

wherein the ratio of the triethanolamine to the bis(trialkoxysilylalkyl) polysulfide is less than 2.0 moles of the triethanolamine per 1 mole of the bis(trialkoxysilylalkyl) polysulfide, and wherein the bis(trialkoxysilylalkyl) polysulfide and the triethanolamine are heated in the presence of an alkali metal alcoholate used in a catalytic quantity, thus substituting a part of the Si-bonded $(OR^1)_3$ groups of the bis(trialkoxysilylalkyl) polysulfide with a group represented by the formula: $(OCH_2CH_2)_3N$.

2. A method for manufacturing a mixture which is liquid at ambient temperature and comprises of a bis(silatranylalkyl) polysulfide represented by the general formula (3):

$$N(CH_2CH_2O)_3SiRS_xRSi(OCH_2CH_2)_3N \quad (3)$$

wherein R is an alkylene group having 1 to 10 carbon atoms, and "x" is a number from 2 to 8, a (silatranylalkyl) (trialkoxysilylalkyl) polysulfide represented by the general formula (4):

$$N(CH_2CH_2O)_3SiRS_xRSi(OR^1)_3 \quad (4)$$

wherein R and "x" are the same as defined above, and $R^1$ is an alkyl group having 1 to 4 carbon atoms, and a bis(trialkoxysilylalkyl) polysulfide represented by the general formula (1):

$$(R^1O)_3SiRS_xRSi(OR^1)_3 \quad (1)$$

wherein R, R¹, and "x" are the same as defined above, the method being characterized by heating a bis(trialkoxysilylalkyl) polysulfide represented by the general formula (1):

(R¹O)₃SiRS$_x$RSi(OR¹)₃ (1)

wherein R, R¹, and "x" are the same as defined above, and a triethanolamine represented by the formula (2):

(HOCH₂CH₂)₃N (2)

wherein the ratio of the triethanolamine to the bis(trialkoxysilylalkyl) polysulfide is less than 2.0 moles of the triethanolamine per 1 mole of the bis(trialkoxysilylalkyl) polysulfide, and wherein the bis(trialkoxysilylalkyl) polysulfide and the triethanolamine are heated in the presence of an alkali metal alcoholate used in a catalytic quantity, thus substituting a part of the Si-bonded (OR¹)₃ groups of the bis(trialkoxysilylalkyl) polysulfide with a group represented by the formula: (OCH₂CH₂)₃N.

3. A mixture which is liquid at ambient temperature and comprises a bis(silatranylalkyl) polysulfide represented by the general formula (3):

N(CH₂CH₂O)₃SiRS$_x$RSi(OCH₂CH₂)₃N (3)

wherein R is an alkylene group having 1 to 10 carbon atoms, and "x" is a number from 2 to 8, and a (silatranylalkyl)(trialkoxysilylalkyl) polysulfide represented by the general formula (4):

N(CH₂CH₂O)₃SiRS$_x$RSi(OR¹)₃ (4)

wherein R and "x" are the same as defined above, and R¹ is an alkyl group having 1 to 4 carbon atoms.

4. A mixture which is liquid at ambient temperature and comprises of a bis(silatranylalkyl) polysulfide represented by the general formula (3):

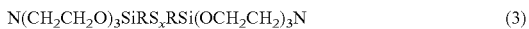
N(CH₂CH₂O)₃SiRS$_x$RSi(OCH₂CH₂)₃N (3)

wherein R is an alkylene group having 1 to 10 carbon atoms, and "x" is a number from 2 to 8, a (silatranylalkyl)(trialkoxysilylalkyl) polysulfide represented by the general formula (4):

N(CH₂CH₂O)₃SiRS$_x$RSi(OR¹)₃ (4)

wherein R and "x" are the same as defined above, and R¹ is an alkyl group having 1 to 4 carbon atoms, and a bis(trialkoxysilylalkyl) polysulfide represented by the general formula (1):

(R¹O)₃SiRS$_x$RSi(OR¹)₃ (1)

wherein R, R¹, and "x" are the same as defined above.

5. A rubber composition comprising:
100 parts by weight of an uncured organic rubber (A),
5.0 to 150 parts by weight of a silica filler (B), and
the mixture (C) claimed in claim 3 which is contained in an amount of 0.1 to 50 wt. % of the weight of component (B).

6. A rubber composition comprising:
100 parts by weight of an uncured organic rubber (A),
5.0 to 150 parts by weight of silica filler (B),
0.1 to 80 parts by weight of carbon black (D), and
the mixture (C) claimed in claim 3 which is contained in an amount of 0.1 to 50 wt. % of the total weight of components (B) and (D).

7. A method for manufacturing as set forth in claim 1 wherein the alkali metal alcoholate is used in an amount of 0.1 to 5.0 mole % per 1 mole of the bis(trialkoxysilylalkyl) polysulfide represented by the general formula (1).

8. A method for manufacturing as set forth in claim 2 wherein the alkali metal alcoholate is used in an amount of 0.1 to 5.0 mole % per 1 mole of the bis(trialkoxysilylalkyl) polysulfide represented by the general formula (1).

9. A mixture as set forth in claim 3 wherein the alkali metal alcoholate is used in an amount of 0.1 to 5.0 mole % per 1 mole of the bis(trialkoxysilylalkyl) polysulfide represented by the general formula (1).

10. A mixture as set forth in claim 4 wherein the alkali metal alcoholate is used in an amount of 0.1 to 5.0 mole % per 1 mole of the bis(trialkoxysilylalkyl) polysulfide represented by the general formula (1).

11. A rubber composition comprising:
100 parts by weight of an uncured organic rubber (A),
5.0 to 150 parts by weight of a silica filler (B), and
the mixture (C) claimed in claim 4 which is contained in an amount of 0.1 to 50 wt. % of the weight of component (B).

12. A rubber composition comprising:
100 parts by weight of an uncured organic rubber (A),
5.0 to 150 parts by weight of silica filler (B),
0.1 to 80 parts by weight of carbon black (D), and
the mixture (C) claimed in claim 4 which is contained in an amount of 0.1 to 50 wt. % of the total weight of components (B) and (D).

* * * * *

UNITED STATES PATENT AND TRADEMARK OFFICE
CERTIFICATE OF CORRECTION

PATENT NO. : 8,093,323 B2
APPLICATION NO. : 12/522835
DATED : January 10, 2012
INVENTOR(S) : Takeaki Saiki, Makoto Iwai and Anil Kumar Tomar It is certified that error appears in the above-identified patent and that said Letters Patent is hereby corrected as shown below:

Title Page
Item (73) Assignee:

Delete:
"DOW CORNING TORAY COMPANY, LTD.     CHIYODA-KU, TOKYO, JAPAN"

Insert:
-- DOW CORNING CORPORATION         MIDLAND, MICHIGAN --
-- DOW CORNING TORAY COMPANY, LTD.     CHIYODA-KU, TOKYO, JAPAN --

Signed and Sealed this
Eleventh Day of June, 2013

Teresa Stanek Rea
*Acting Director of the United States Patent and Trademark Office*